United States Patent [19]

Strongwater

[11] Patent Number: 5,391,418
[45] Date of Patent: Feb. 21, 1995

[54] METHOD AND APPARATUS FOR PRODUCING MATTRESS PADS AND THE LIKE

[75] Inventor: Bruce Strongwater, Englewood, N.J.

[73] Assignee: J. Lamb, Inc., Englewood, N.J.

[21] Appl. No.: 76,246

[22] Filed: Jun. 11, 1993

[51] Int. Cl.6 .......................... B32B 5/26; B32B 7/10
[52] U.S. Cl. ................... 428/171; 428/196; 428/198; 428/286
[58] Field of Search ............ 428/196, 198, 286, 287, 428/171

[56] References Cited

U.S. PATENT DOCUMENTS

| | | | |
|---|---|---|---|
| 2,816,054 | 12/1957 | Howden | 428/198 |
| 2,964,441 | 12/1960 | Goldstone | 428/171 |
| 4,379,192 | 4/1983 | Wahlquist | 428/198 |
| 4,595,629 | 6/1986 | Mays | 428/286 |
| 4,725,473 | 2/1988 | Van Gompel | 428/198 |
| 4,844,965 | 7/1989 | Foxman | 428/198 |

*Primary Examiner*—Jenna L. Davis
*Attorney, Agent, or Firm*—Louis Weinstein

[57] ABSTRACT

Method and apparatus for producing a bed covering or the like comprised of a first thermoplastic web, a pair of fibrous mats of substantial loft, said web and mats being bonded together in accordance with a quilted pattern utilizing a thermoelectric bonding technique. The bonding layer, which is preferably polyurethane or a derivative thereof, forms an excellent bond with both the web and the fibrous mats. The fibrous mats provide excellent moisture absorbency and are breathable since the fibrous mats are bonded to the web only at the limited areas defined by the pattern. The first web provides an excellent waterproof barrier, while the mat provides an array of puffed-up regions each delineated by the bonding pattern to yield and aesthetically appealing cover which may be used with either fibrous web exposed.

10 Claims, 2 Drawing Sheets

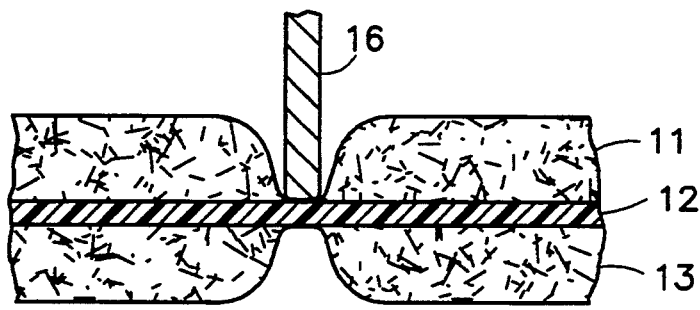
Fig. 2
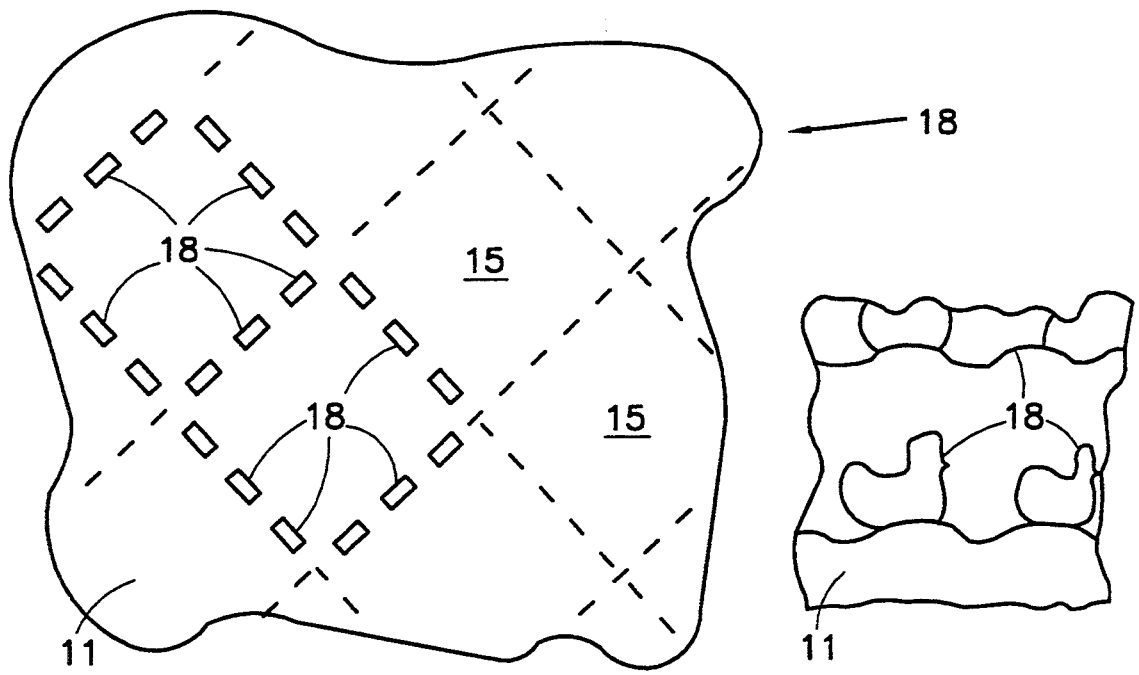
Fig. 2a
Fig. 2b
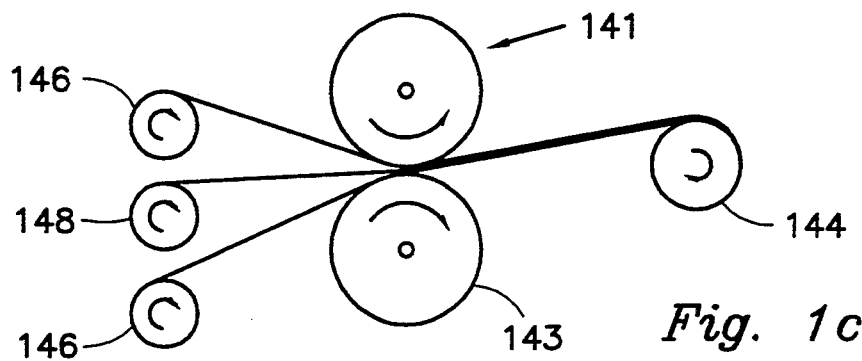
Fig. 1c

METHOD AND APPARATUS FOR PRODUCING MATTRESS PADS AND THE LIKE

FIELD OF THE INVENTION

The present invention relates to mattress and bed pads and the like and more particularly to a novel method and apparatus for producing mattress pads, bed pads and the like having a moisture barrier surface, a pair of moisture absorption surfaces having an aesthetically pleasing quilted appearance and being highly serviceable so as to withstand repeated washings.

BACKGROUND OF THE INVENTION

Some bedcovers such as, for example, mattress pads are typically designed to have a substantially waterproof major surface with the remaining major surface having at lest some moisture absorbency. Conventional pads, which are typically cotton/polyester pads having a waterproof major surface sealed thereto by a pinsonic technique, are disadvantageous for the reasons that the joining technique produces holes in the goods destroying the effectiveness of the water and/or moisture barrier and the seals formed through the use of the aforesaid joining technique are extremely poor quality so that the cotton/polyester pad is incapable of withstanding as few as several washings without seriously degrading the seals.

It is also conventional to form such pads and join their plurality of layers by sewing the layers together. The sew lines form a stitched or quilted design. The latter design has the distinct disadvantage of not being waterproof and of being quite labor intensive and hence expensive to produce. In addition, the stitched pattern degrades after several washings and even a single defective stitch causes the entire stitched pattern to come apart.

BRIEF DESCRIPTION OF THE INVENTION

The present invention provides a bed covering preferably in the form of a mattress pad having exposed major surfaces which are respectively substantially waterproof and moisture absorbent as well as being breathable. The structure further includes a mat-like layer of fibrous material preferably comprised of non-woven loosely held interengaging fibers which provide the pad with puffed or raised areas, each surrounded by the lines of the quilt pattern to yield an aesthetically pleasing quilted effect.

The webs forming the outer exposed major surfaces are bonded by way of an intermediate layer to create a unified end product in which the major surfaces are bonded together through an intermediary bonding web to form a finished product having all of the advantages of conventional pads as well as providing a highly serviceable end product capable of withstanding numerous washings without suffering any degradation.

The preferred embodiment is comprised of a plurality of webs which include, in the order of alignment, a waterproof web formed of a plastic material; and a pair of fibrous mats of non-woven material having a substantial loft and excellent moisture absorbency qualities and capable of forming a good bond with the waterproof web which serves as a bonding web for both outer layers.

A first web is preferably formed of a plastic material such as a vinyl or polyvinyl having the capabilities of providing a waterproof barrier (or at least a vapor barrier) and forming a bond capable of withstanding numerous washings without degrading the integrity of the bond or the webs.

The first web is preferably comprised of a vinyl such as, for example, a web comprised of at least one material selected from vinyl chloride polymer resins, thermoplastic polyester resins, vinylidene chloride polymer resins, polyamide resins and other materials having the properties of being waterproof and forming a good bond with the bonding web.

The non-woven outer layers are preferably formed of synthetic organic thermoplastic fibers having substantial loft to provide an aesthetically appealing quilted pad and forming a good bond with the adjacent webs. The bonds, as well as the mat, are capable of retaining the aforementioned characteristics even after numerous washings.

The waterproof layer is formed of a plastic material which softens and is sufficiently activated during the bonding process to form an excellent bond with the adjacent layers while at the same time retaining its integrity as a vapor barrier and preferably a waterproof barrier which further contributes to the aesthetically appealing high loft appearance of the quilted product due to the air captured between the moisture barrier and the absorbent layers.

The outer layers are preferably identical and are formed of a non-woven material of high quality and having good moisture absorption characteristics while at the same time forming a good bond with the vapor barrier. The fabric may be a blend of natural and synthetic fibers such as, for example, cotton and polyester. As an alternative, the fabric layer may be a non-woven fabric such as a viscose non-woven fabric.

The product may be produced in a substantially continuous fashion wherein each of the webs are wound about supply reels or the like and are introduced into dielectric heating apparatus in the form of continuous webs of indeterminate length which are superimposed one upon the other as they move through the heating apparatus.

The dielectric apparatus may be comprised of a platen electrode and a die electrode in the configuration of the pattern to be formed. The outer non-woven webs respectively engage the platen electrode and the die electrode. The die is mounted to reciprocate and is pressed into the aforementioned superimposed webs. High frequency electrical energy is coupled to the electrodes which dielectrically heat the materials pressed between the die and platen electrodes. The heating cycle is comprised of a sealing phase having a duration in the range from two to four seconds followed by a cooling phase of one to two seconds during which the electrodes and bonded webs are cooled by use of a coolant flowing through the electrode members and thereafter followed by a laminate advance phase of the order of 0.5 to one second during which time the die electrode is displaced from the platen electrode and the bonded webs are advanced, preferably by reciprocating gripper assemblies, through a distance sufficient to move beyond the electrodes and to introduce the next adjacent portions of the superimposed webs to the compression and heating cycle. The cooling cycle is utilized to set the bond and to prevent the waterproof web from sticking to the die electrode. As an alternative, the quilting pattern may be provided by a roller of suitable diameter so as to repeat the quilted pattern every eighteen inches or twenty-four inches, for example.

The dielectric heating apparatus provides electrical energy in the megacycle range with the dissipated energy being of the order of tens of kilowatts.

The product may, alternatively be provided with a fabric layer on both exposed surfaces thereof, the first web serving as both a waterproof layer as well as a bonding layer.

Product comprising the layers of material set forth hereinabove and being formed in accordance with the method steps described hereinabove exhibit all of the desired characteristics of conventional covers while providing the unique advantages of excellent moisture absorbency and waterproof qualities in an aesthetically appealing bed cover wherein the bonds joining the several webs comprising the product do not deteriorate even after repeated washing. Either outer surface may serve as the exposed surface of the product when placed on a bed or other supporting surface.

OBJECTS OF THE INVENTION

It is therefore one object of the present invention to provide a novel method and apparatus for producing an aesthetically pleasing quilted product having major surfaces exhibiting the qualities of excellent moisture absorption and having a moisture barrier layer in which the bonds joining said layers are able to withstand repeated washing without deterioration.

Another object of the present invention is to provide a novel product for use as a covering for a bed or the like and having respective major surfaces exhibiting the qualities of good moisture absorption along both major surfaces and wherein the layers comprising the product are joined along bond lines which provide an aesthetically appealing quilted product with the layers being bonded along the lines defining the quilted pattern, said bonds being capable of withstanding numerous washings without deterioration.

The above, as well as other objects of the present invention will readily become apparent when reading the accompanying description and drawing in which:

BRIEF DESCRIPTION OF THE FIGURES

FIG. 1c shows an alternative apparatus for forming the product of the present invention;

FIG. 2 shows a sectional view of the novel, highly advantageous product formed through the use of the apparatus shown in FIGS. 1a and 1b; and FIGS. 2a and 2b show plan views of the product shown in FIG. 2.

DETAILED DESCRIPTION OF THE INVENTION AND PREFERRED EMBODIMENTS THEREOF

Figure 1B:
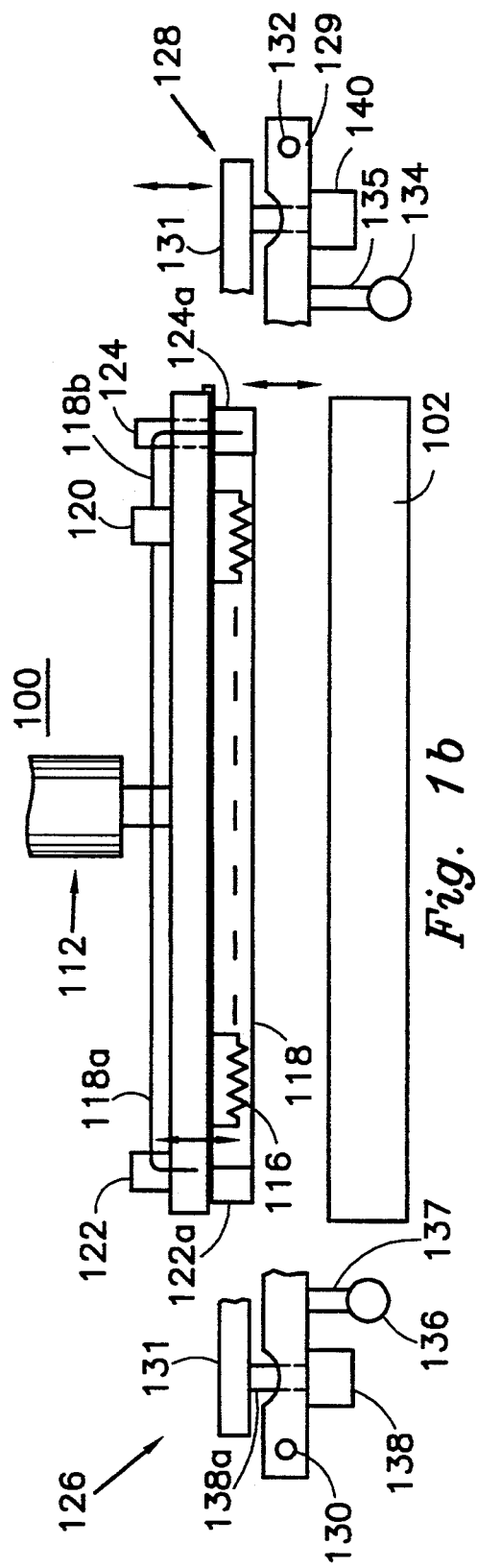
FIGS. 1a and 1b show the side and end elevational views, respectively of the apparatus employed for forming the product of the present invention.

FIGS. 2, 2a and 2b shows use of the product 10 embodying the principles of the present invention and being comprised of a fibrous mat 11, a waterproof bonding layer 12, and a second fibrous mat 13.

Layer 12 is comprised of a plastic material which exhibits the characteristics of being waterproof and being capable of being bonded to the mats 11 and 13 and is capable of forming an excellent bond therebetween.

Suitable materials include polyethylene vinyl, polyvinyl chloride, vinyl chloride polymer resins, thermoplastic resins, vinylidene chloride polymer resins and polyamide resins.

The mats 11 and 13 serve as wadding having substantial loft to create puffed regions 15, each surrounded by and defined by the pattern lines 18 created initially by the die electrode configuration which is pressed against web 12 and which pattern is permanently retained upon dielectric heating of the product 10. A portion 16 of the die electrode is shown pressed into the webs forming the product.

The wadding forming mats 11 and 13 comprises a fibrous mat-like member formed of fibers such as a lofty, resilient, non-woven fibrous mat or fiberfill or scrim. The wadding may be formed of any suitable fiber. However, the preferred fibers are synthetic organic thermoplastic fibers preferably exhibiting relatively high dielectric loss factors when exposed to the high frequency fields generated by the dielectric heating equipment (shown in FIGS. 1a, 1b) in order to permit rapid bonding as well as providing strong bonds. Examples of synthetic fibers include acrylic and modacrylic, such as those formed by polymerized acrylonitrile With the nitrile polar groups spaced along the molecule, and polymerized acrylonitrile and vinyl chloride, having chlorine and nitrile groups along the polymer, polyester, nylon 6 and nylon 66 types of fibers. Polyester fibers are preferably used in whole or in part to great advantage.

The fibers of the wadding are resinated to bond the fibers whose lengths are preferably in the range from one to three inches. The resin may be a polyvinyl chloride or polyvinyl chloride in combination with another resin, such as urethane. Thermosetting resins may be used in combination with thermoplastic fibers to enhance the washability of the wadding layers 12 and 14, if desired.

The mat may be produced with conventional equipment such as a Garnett or a Curlator Rando Web Machine forming the web with fibers preferably chosen from those listed hereinabove. Polyester fiber may, however, be used in whole or in part to great advantage.

The binder may be of a polyvinyl chloride, polyvinyl acetate, urethane, acrylic or nitrile type, such as acrylonitrile, or a combination of these materials.

Webs 11 and 13 also provide softness and absorbency. Since either web 11 or 13 may contact the skin, it is desirable to use a comfortable, non-irritating material. One desired fabric is a cotton/polyester blend with the blend ratio (in weight percent) being cotton 65 percent to 45 percent and polyester 35 percent to 55 percent with the preferred ratio being cotton 50 percent, polyester 50 percent. The aforementioned blend is comprised of a woven fabric made up of the aforementioned materials. Alternatively, the fabric may be a 100 percent cotton fabric which is treated with a resin which may be polyester or a resin having the characteristics of polyester. The webs 11 and 13, in addition to having excellent moisture absorbency, are breathable since they are bonded to web 12 only along the lines 18 of the quilt pattern (see FIG. 2a). The webs 11 and 13 may also be pretreated to reduce shrinkage.

As an alternative, webs 12 and 14 may be a non-woven fabric having the bonding and washability qualities of the cotton or cotton/polyester blend descried above. The non-woven fabric may be a viscose non-woven fabric containing a resin binder and calendared to provide a flat web similar in appearance to the cotton or cotton/polyester woven fabric.

The bonding layer 12 serves to bond the layers 11 and 13. Web 12 may be impermeable or alternatively may be permeable to moisture, enabling the wadding of layers 11 and 13 to contribute to the absorbency characteristics of the end product. The web 12 is preferably formed of a urethane or polyurethane material which provides an excellent bond between the outermost webs 11 and 13. A web 12 having an impervious characteristic provides a good waterproof bond.

As an alternative to the webs 11 and 13, webs 11 and 13 may be substituted by an impregnated fiber scrim or thermoplastic scrim with the impregnate being acrylic, polyvinyl chloride, polyvinyl acetate, a polyamide, such as a nylon, a polyurethane, or a polyester.

The quilted patterns may take any form, the patterns of FIGS. 2a and 2b being merely exemplary.

Figure 1A:
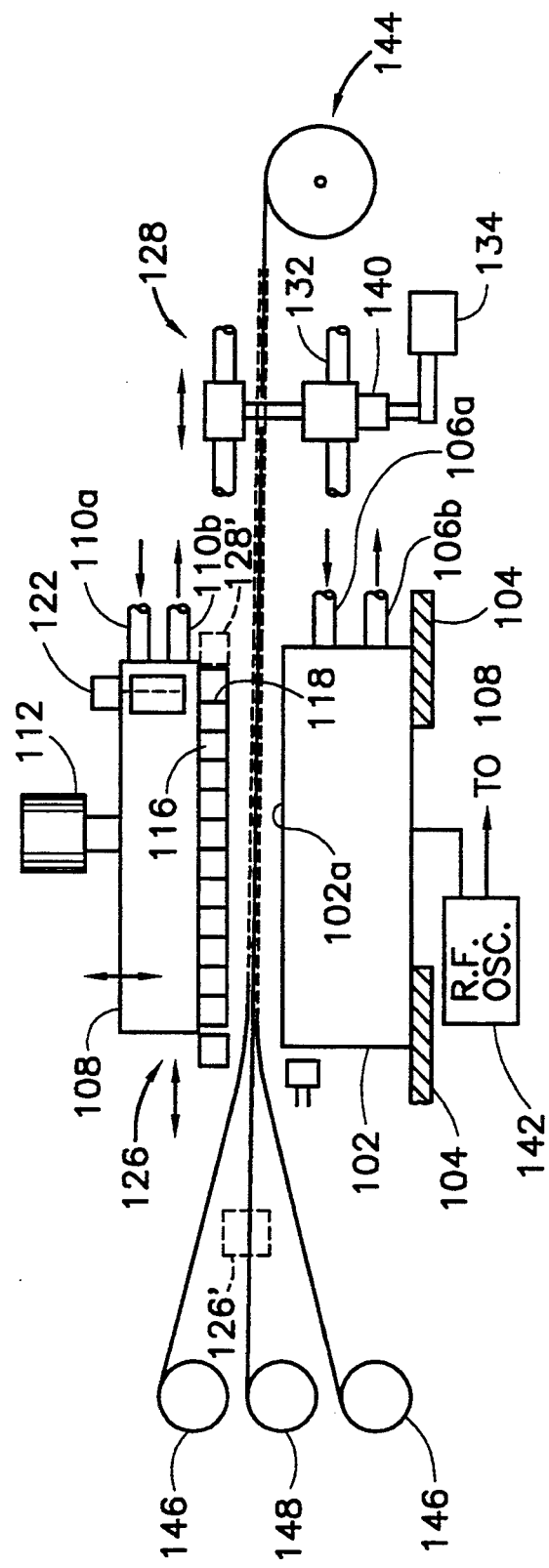

The apparatus utilized to form the finished product is shown in FIGS. 1a and 1b and is comprised of dielectric heating apparatus 100 which has been shown in simplified form for purposes of simplicity and brevity.

A stationary platen electrode 102 is mounted upon support frames shown in simplified fashion as 104. The top surface 102a of platen 102 is planar and, in the preferred embodiment, engages and supports web 13. Platen 102 is provided with cooling tubes (not shown) coupled to conduits 106a, 106b which respectively introduce and remove a coolant which is selectively passed through platen 102 during the cooling phase of each operating cycle, as will be more fully described.

A reciprocating electrode 108 having downwardly projecting die portion 116 is mounted for reciprocal movement under control of a hydraulic cylinder assembly 112. The electrode pattern 116, one portion thereof 16 being shown in FIG. 2, forms the aesthetically pleasing quilted pattern 18 shown in FIGS. 2a and 2b in a manner to be more fully described. The die pattern 116 is integrally mounted to and extends downwardly from member 108 which is provided with circulating tubes (not shown) coupled with a coolant source (not shown) and having conduits 110a, 110b for introducing coolant into and withdrawing coolant from electrode 108 to cool the die pattern 116 during the cooling phase of an operating cycle. The member 108 and die pattern 116 are moved vertically downward to firmly press the die pattern into the webs in the manner shown best in FIG. 2, whereupon a heating cycle is initiated. Upon completion of the heating cycle and the cooling cycle, the electrode members 108 and 116 are moved vertically upward to allow the now bonded webs to be advanced beneath the cooperating electrodes for dielectrically heating the next unbonded portion of these webs.

An elongated substantially rigid, high resistance wire 118 is mounted parallel to and to the right of the die pattern 116. Wire 118 is coupled to an electrical energy source 120 which selectively energizes wire 118. Wire 118 has a relatively high resistance and is designed to be heated sufficiently to form a "hot cut" in the plastic materials forming the end product to identify predetermined lengths of finished product and thereby facilitate and simplify the separation of said predetermined lengths in a manner to be more fully described. Wire 118 is mounted in a reciprocating fashion and is driven either vertically downward or vertically upwardly by hydraulic assemblies 122,124 for being respectively pressed into and displaced from the product being formed. The electrical lines 118a, 118b electrically coupling wire 118 to power source 120 are electrically insulated from the hydraulic cylinder assemblies 122, 124 and from the mounts 122a, 124a.

A pair of gripping assemblies 126, 128 are utilized to advance the webs after the reciprocating electrode 108 is lifted upwardly to advance the finished product toward the right relative to FIG. 1a and to introduce the next portion of the webs to be bonded between the cooperating electrodes. Since the gripping assemblies are the same in both design and function, only one of these assemblies will be described in detail, for purposes of simplicity.

Gripping assembly 128 is comprised of elongated bar 129, which is guided for reciprocating movement by a pair of spaced parallel rods 130, 132 and is moved in reciprocating fashion by hydraulic cylinder assemblies 134, 136 each coupled to bar 129 by members 135, 137. A cooperating upper gripper bar 131 is mounted in a reciprocating fashion and is moved selectively up and down by a pair of hydraulic cylinder assemblies 138, 140 which have their piston rods 138a, 140a joined to gripper bar 131. The gripper assembly 126 is similar in design and function to the gripper assembly 128 and for that reason, a description thereof will be omitted for purposes of brevity.

The electrodes 102 and 108 are electrically connected to an RF oscillating source 142 for providing RF energy of the desired frequency and energy level to achieve good bonding between and among the various webs as will be more fully described.

Let it be assumed that a heating and tooling phase have been completed and that the electrode 108 has been moved vertically upward. At this time, the gripper assemblies occupy the positions 126', 128'. The hydraulic cylinder assemblies of gripper bar assembly 128 lowers bar 131 to grip the finished product between bars 131 and 129. Gripper assembly 126 operates in a similar manner. With the webs being gripped in this manner by assemblies 126, 128, the hydraulic cylinders 134, 136 are operated to move gripper assembly 128 toward the right relative to FIG. 1a from position 128' to position 128. Similar hydraulic assemblies (not shown) forming part of the gripper assembly 126 move the latter gripper assembly from dotted line position 126' to the solid line position 126, thereby advancing the webs to the next unbonded portion thereof to be dielectrically heated. When the gripper assemblies 126, 128 have been advanced to the solid line positions 126, 128, hydraulic assembly 112 moves the reciprocating electrode 108 downwardly, pressing the die pattern 116 firmly into the webs so as to assume the shape shown in FIG. 2.

After the electrode 108 has been moved into the aforementioned position in readiness for the dielectric heating phase, the gripper assemblies 126 and 128 are opened by upward movement of their upper rods and are moved to the left to occupy the dotted line positions 126', 128'. Thereafter, the gripping assemblies are moved to the gripping position by lowering the upper gripper members.

As soon as the reciprocating electrode 108 has been moved to the operative position, RF energy is applied to the electrodes 102, 108 to dielectrically heat the compressed areas of the webs between the lower ends 16a of the die pattern and the top surface 102a of platen electrode 102. The RF oscillator 142 which, in the preferred embodiment, operates in a frequency range of between 15 and 40 Mhz generates energy in the region of from 20 to 40 kilowatts. The sealing phase occurs during a time interval of two to four seconds D. At the end of the heating phase, the RF energy source is deenergized.

Coolant is then urged through the cooling tubes of the electrodes 102, 108 to remove the heat transferred to the platen and die electrodes 102, 116 during the sealing operation. The cooling phase has a duration in the range of from one to two seconds. The cooling phase lowers the temperature of the electrodes as well as the bonded webs to a level sufficient to set the bond and prevent the outer webs from sticking to the electrodes.

Upon completion of the cooling phase, hydraulic cylinder assembly 112 lifts the reciprocating electrode 108 upwardly and away from the finished product whereupon the gripper assemblies are again moved from the dotted line position 126', 128' to advance the next portion of the webs into the dielectric heating apparatus. The advancement phase is performed during a one second interval. The advancement of the webs by the gripper assemblies 126, 128 may be initiated as soon as the reciprocating electrode 108 has cleared the vinyl web 11. This permits the time of the operating cycle to be reduced. In the preferred embodiment, the equipment is capable of performing of the order of twenty-five operating cycles per minute, each cycle being comprised of heating, cooling and web advancing phases.

The operating members 122, 124 selectively move cutting wire 118 downwardly after a predetermined number of operating cycles have been completed. For example, in one embodiment, the wire 118 is urged against the web being formed at seventy-seven inch intervals which occurs every sixth operating cycle in order to define one bed cover.

The finished product is wound upon a takeup spool 144. The wire 118, although forming a "hot cut" in the finished product, does not completely sever the finished product. Thus the take-up spool is removed at the end of a run, i.e. when the supply spools 146, 148, 150 and 152 are exhausted, enabling the individual covers to be separated from one another at a location separate and remote from the dielectric heating installation to reduce the overall production time. The electrical source 120 is energized to introduce current into wire 118 and thereby heat the wire to form the "hot cut" in the finished product. Although the electric wire 118 is preferably shown located at the right-hand end of the dielectric heating assembly shown relative to FIG. 1a, the wire 118 and associated apparatus may be positioned at some other location relative to die 118, if desired.

The die pattern may be comprised of discontinuous bond lines 118 as shown in FIG. 2a or may be comprised of continuous bond lines in the case where each puffed region 15 is desired to be sealed to capture and seal air within each region.

As an alternative, the platen 102 and electrode 108 may be rollers 143, 141 respectively. The quilted pattern is provided upon the periphery of roller 141. The electrical connections and Cooperating equipment may be similar to that shown in FIGS. 1a and 1b and have been omitted for purposes of simplicity. The repeat of the pattern is a function of the diameter of roller 141.

A finished product formed of the materials and produced in the process described hereinabove has been found to meet the following requirements:

1. The ability to withstand dryer temperatures of at least 205° F. without harming the materials and/or the bonds of the finished product.
2. Is autoclavable, i.e. is capable of withstanding 15-30 PSIG steam.
3. Experiences no more than a two percent weight loss in soapy water extraction.
4. Is waterproof and fire retardant, withstands water temperatures of at least 205° F. without degrading.
5. Has a tensile strength of 2100 PSI minimum in both direction and a minimum elongation of 150 percent.
6. Meets all requirements of the Flammable Fabrics Act, is electronically sealable, has no tackiness and complies with all specifications imposed upon manufacturers in the bedding industry.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

What is claimed is:

1. A washable quilted reversible laminate produced according to the following method comprising the steps of:

(a) providing a first web of a thermoplastic film material to provide a moisture barrier layer;
   (b) placing second and third webs of a non-woven fibrous material having intermingled fibers for absorbing and retaining moisture into engagement with opposite major surfaces of said first web;
   (c) placing the aforementioned engaging webs within a dielectric heating assembly comprised of a conductive backing platen electrode and a die electrode having a predetermined pattern;
   pressing said die pattern into an exposed major surface of one of said fibrous webs to thereby firmly press together those portions of said fibrous webs beneath said die pattern against said first web in accordance with said die pattern while allowing said fibrous webs not compressed between said die and said platen to remain in their uncompressed state; and
   (e) applying electrical energy across said die and said platen to dielectrically heat the compressed portions sufficient to compress and bond said fibrous webs to said web to form an aesthetically appealing pattern on both exposed major surfaces of said fibrous webs, said bond being capable of withstanding repeated washing, without destroying the bonds.

2. A washable quilted reversible laminate for use as a cover comprising:

a first web of a thermoplastic film material for providing a moisture barrier and having opposing major surfaces;
   a pair of non-woven fibrous mats of intermingled fibers each having one major surface engaging one major surface of said first web;
   said mats being formed of a material for absorbing and retaining moisture;
   portions of said fibrous mats being firmly pressed against and dielectrically bonded to associated portions of said first web in accordance with a predetermined aesthetically appealing pattern so that portions of said mats aligned with said pattern are compressed against said first web while the remaining portions of said mats are uncompressed and remain in an uncompressed state so that the uncompressed portions of the cover are in a puffed up state;

said bonds forming a quilted pattern on exposed major surfaces of said cover, retaining said fibrous mats compressed against said first web and said cover being capable of withstanding repeated washing, without destroying said bonds and being usable as a cover with either opposed major surface exposed.

3. The cover of claim 2 wherein said first web comprises a sheet of material taken from the group consisting of polyethylene, vinyl, polyvinyl chloride, vinyl chloride polymer, and polyamide resins.

4. The cover of claim 2 wherein said second and third mats each comprises a blend of materials whose major constituent is one of the materials taken from the group consisting of urethane and polyurethane.

5. The cover of claim 2 wherein said fibrous mats are formed of a thermoplastic material.

6. The cover of claim 5 wherein said thermoplastic material of said mats is comprised of scrim impregnated with one of the materials taken from the group consisting of acrylic, acrylonitrile, polyvinyl chloride, polyvinyl acetate, polyester, polyurethane and nylon.

7. The cover of claim 6 wherein said thermoplastic material of said mats comprises fibers impregnated with a thermosetting resin to enhance the washability of the fibrous met.

8. The cover of claim 7 wherein said scrim is comprised of non-woven fibers.

9. The cover of claim 8 wherein said fibers are formed of thermoplastic material and each have a length in the range from one to three inches.

10. The cover of claim 3 wherein said thermoplastic sheet of material provides a waterproof barrier.

* * * * *

UNITED STATES PATENT AND TRADEMARK OFFICE
CERTIFICATE OF CORRECTION

PATENT NO. : 5,391,418
DATED : FEBRUARY 21, 1995
INVENTOR(S) : BRUCE STRONGWATER

It is certified that error appears in the above-indentified patent and that said Letters Patent is hereby corrected as shown below:

```
Column 1, line 19, change "lest" to --least--.
Column 4, line 22, change "With" to --with--.
Column 4, line 63, change "webs 12 and 14" to --webs 11
          and 13--.
Column 4, line 65, change "descried" to --described--.
Column 6, line 31, change "tooling" to --cooling--.
Column 7, line 57, change "Cooperating" to --cooperating--.
Column 8, line 14 of Claim 1, before "pressing" insert
          --(d)--.
Column 8, line 25 of Claim 1, before "web" insert --first--.
```

Signed and Sealed this

Twenty-third Day of May, 1995

Attest:

BRUCE LEHMAN

*Attesting Officer*    *Commissioner of Patents and Trademarks*